US006744245B2

(12) United States Patent
Taylor et al.

(10) Patent No.: US 6,744,245 B2
(45) Date of Patent: Jun. 1, 2004

(54) PARTICLE COUNT CORRECTION METHOD AND APPARATUS

(75) Inventors: Richard Lee Taylor, Cooper City, FL (US); Min Zheng, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/917,453

(22) Filed: Jul. 27, 2001

(65) Prior Publication Data

US 2003/0020447 A1 Jan. 30, 2003

(51) Int. Cl.[7] .................. G01N 27/00; G01N 31/00; G06M 11/04
(52) U.S. Cl. .................. 324/71.4; 377/11; 702/26
(58) Field of Search .................. 324/71.4; 377/11; 702/26, 29

(56) References Cited

U.S. PATENT DOCUMENTS

| | | | |
|---|---|---|---|
| 4,021,117 A | * 5/1977 | Gohde et al. | 356/39 |
| 4,090,129 A | * 5/1978 | Gear | 324/71.1 |
| 4,110,604 A | * 8/1978 | Haynes et al. | 377/10 |
| 4,251,768 A | * 2/1981 | Angel et al. | 377/11 |
| 4,303,337 A | * 12/1981 | James et al. | 356/72 |
| 4,447,883 A | * 5/1984 | Farrell et al. | 324/71.4 |
| 4,580,093 A | 4/1986 | Feier et al. | 324/71.4 |
| 4,977,517 A | 12/1990 | Gibbs et al. | 702/51 |
| 4,981,580 A | 1/1991 | Auer | 209/3.1 |
| 5,039,935 A | 8/1991 | Hachey et al. | 324/71.4 |
| 5,247,461 A | * 9/1993 | Berg et al. | 324/464 |
| 5,353,937 A | 10/1994 | Childress | 209/563 |
| 5,437,200 A | 8/1995 | Hollinger | 73/863.73 |
| 5,452,237 A | * 9/1995 | Jones, Jr. | 702/26 |
| 5,643,796 A | 7/1997 | Van den Engh et al. | 436/50 |
| 6,119,510 A | * 9/2000 | Carasso et al. | 73/61.75 |
| 6,122,599 A | 9/2000 | Mehta | 702/100 |
| 6,259,242 B1 | * 7/2001 | Graham et al. | 324/71.4 |
| 6,275,290 B1 | * 8/2001 | Cerni et al. | 356/335 |

OTHER PUBLICATIONS

Wales, et al., *The Review of Scientific Instruments*, vol. 32, No. 10, pp 1132–1136 (1961).
Princen, et al., *The Review of Scientific Instruments*, vol. 36, No. 5, pp 646–653 (1965).
Wynn, et al., *Powder Technology*, 93, pp 163–175 (1997).

* cited by examiner

*Primary Examiner*—N. Le
*Assistant Examiner*—Timothy J. Dole
(74) *Attorney, Agent, or Firm*—Birch, Stewart, Kolasch & Birch; Mitchell E. Alter

(57) ABSTRACT

A method is disclosed which allows more accurate counting of particles where the sample has significant size variability between particles. The method uses flight time and wait time to obtain a corrected count of particles.

16 Claims, 5 Drawing Sheets

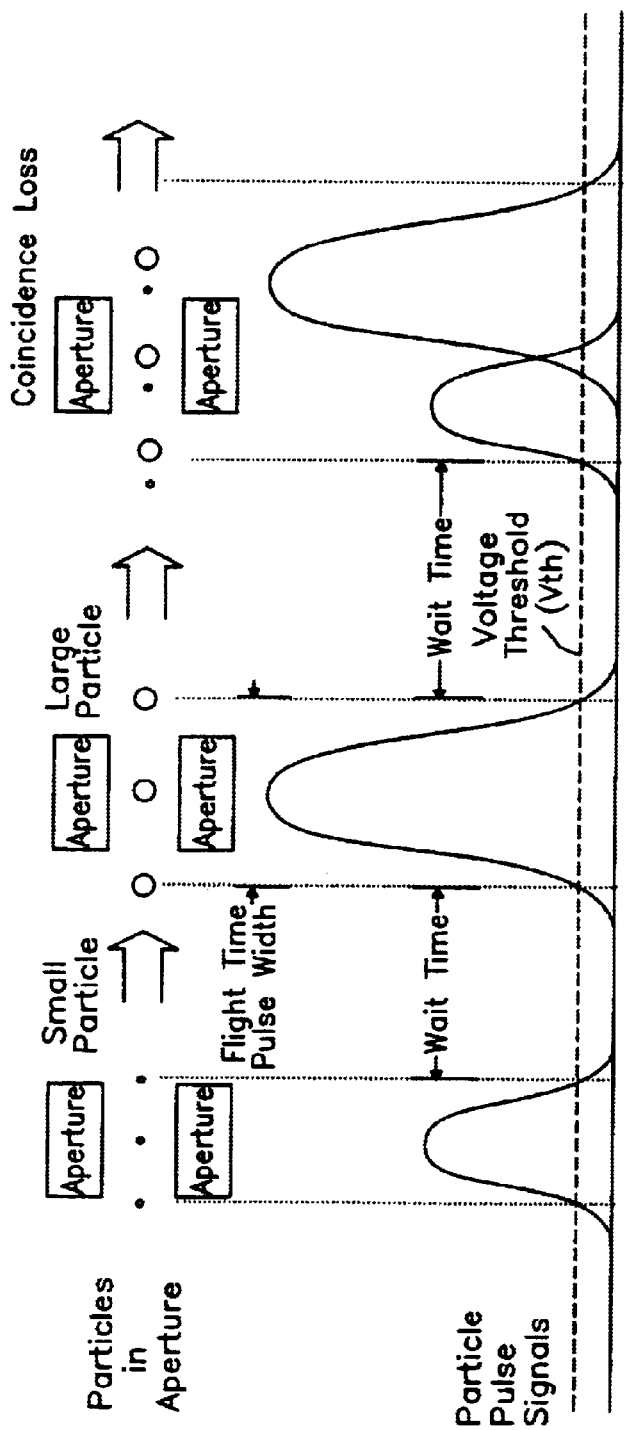
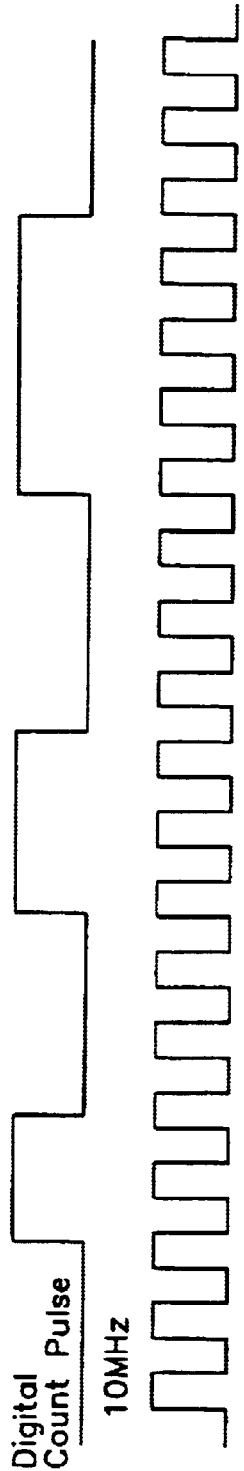
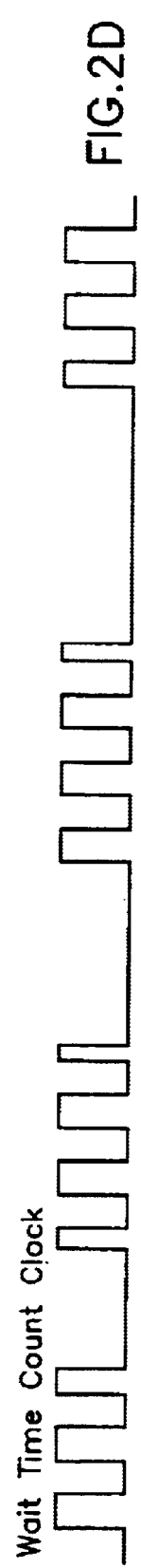

PARTICLE COUNT CORRECTION METHOD AND APPARATUS

BACKGROUND OF THE INVENTION

1. Field of the Invention

The present invention relates to counting of particles. The method is particularly useful in the counting of a sample of particles having a high density and variability in size.

2. Background Art

In many industrial and medical applications there is a need to determine the concentration of particles contained in a liquid sample solution. This sample solution generally contains one type of particle, which is of some minimum size and larger. These particles are counted by passing the sample solution fluid with the particles to be counted through an aperture, which has an electric current passing through it. When these particles go through the aperture an electrical pulse is generated whose peak voltage is proportional to the size of the particle. This analog particle voltage pulse is applied to a comparator circuit, which will generate a +5 volt level particle count pulse when the comparators threshold is exceeded. The particle count pulse signal is normally at 0 volts until the particle crosses the threshold and then goes to +5 volts for as long as the signal is above the threshold and returns to zero volts when the particle is no longer in the aperture sensing zone. This +5 volt particle count pulse then drives a counter, which is incremented for each particle count pulse on the leading or trailing edge.

This counting technique works very well for lower concentration samples but is very inaccurate when high concentration samples are counted. There is a tendency to under count these higher concentration samples. This under counting is mainly caused by particle coincidence in the aperture. Coincidence occurs when more than one particle is sensed in the aperture at the same time, only one particle is counted. This results in undercounting for high concentration samples.

Typically, to correct for this coincidence loss a coincidence correction algorithm is applied to the raw count to improve the count for high concentration samples. One of the most basic and effective statistically derived coincidence correction formulas is (Wynn and Hounslow—Coincidence correction for electrical-zone (COULTER COUNTER®) particle size analyzers, Powder Technology, 93, 163–175 (1997), see, in particular, p. 164, Formula 1. The entire contents of this reference are hereby incorporated by reference).

$$TC = \frac{1}{Z}\ln\left(\frac{1}{1 - Z * RC}\right) \quad (1)$$

TC=True coincidence corrected Count in counts/s
RC=Raw Count
ESV=Effective Sensing Volume in $\mu L$
FR=Flow Rate in $\mu L/s$
Z=ESV/FR in seconds The value of Z is adjusted until the result is linear. Parameter Z is a function of the aperture size, flow rate, and average particle size.

$$FC = TC * (DR/FR) * CF \quad (2)$$

FC=Final Count in Counts/$\mu L$
DR=Dilution Ratio
CF=Calibration Factor

This correction improves the count some but the loss at high concentrations is still too great and at higher concentrations the raw count will not increase with increasing concentration and may even recover lower counts. This coincidence correction formula is no longer effective when this happens. If the raw counts for these very high concentrations could be corrected then that would allow the coincidence correction algorithm to perform better. Another method is needed that will reduce the particle losses for higher concentration samples.

The sample may be further diluted and rerun to reduce the loss and improve the raw count but this will result in reduced lab throughput as the sample has to be run again. The instruments dilution ratio may be increased to reduce the loss and improve the raw count but this will result in longer count times, which will impact the instruments throughput. It also degrades the count accuracy for low count normal samples. This would not be a preferred method to improve the count linearity.

The optimum solution is to achieve an accurate and linear particle count for high and low concentration samples in the shortest amount of time. This is very difficult for some sample types such as white blood cells where the ratio of abnormal to normal cell concentrations is very high (450,000/5,000 or 90 to 1). The dilution is typically low (251 to 1) to improve the throughput and accuracy of white normals. This low dilution makes the high concentration whites very difficult to count.

Another method of count correction is well known in the industry (see U.S. Pat. No. 4,447,883 to Farrell et al, the entire contents of which are hereby incorporated by reference). This method calculates the average time between particles or total wait time of the counted particle stream and sets the corrected count equal to the inverse of the average wait time. The basic theoretical formula is that the frequency or counts per second is equal to the inverse of the average period of the particle pulse stream.

This method assumes that the effects of the aperture size, particle size and flight time can be ignored. This method operates based on the wait time containing information about lost counts due to coincidence. If two particles go through the aperture too close together, then one count is lost. However, the two particles take up to twice as long to go through the aperture. This reduces the Total Wait Time and causes the true count to be increased.

The Total Flight Time as measured in this method is corrupted with numerous coincidence events. Therefore the average flight time cannot be accurately determined from the Total Flight Time divided by the raw count.

The Total Wait Time is an accurate measurement of the time that no particle is present. Therefore the average wait time derived by dividing the Total Wait Time by the raw count is a substantially reliable measurement. Also the Total Weight Time can be calculated by measuring the total flight time and subtracting this from the total count time.

One key parameter is not handled very well in current methods including both methods mentioned above. This is the consideration of the effects that particle size have on proper coincidence correction. Both methods above would not work properly if different size particles were run through the aperture. The coincidence correction method uses a fixed average particle size to determine the effective sensing volume. If the particle size changes from sample to sample then the formula will no longer work properly. The wait time count correction method does not include the true Total Flight Time in the formula. Even though it measures the Total Flight Time it only uses this information to calculate the Total Wait Time. The Total Flight Time as measured is corrupted by coincidence and is not a good measurement of the true flight time. This method also will not perform well with different size particles. This is important for sample types such as white blood cells. White blood cells typically have a wide range of particle sizes. Clearly, the effects of particle size must be included in the correction methods to make them work properly at high concentrations with multiple size particles. Most count systems also generate a size histogram for the particles being counted. The average size of the population counted can be determined from the histogram.

Various methods for coincidence correction are described in Wales and Wilson, The Review of Scientific Instruments, Vol. 32, No. 10, p. 1132–1136 (1961), Princen and Kwolek, The Review of Scientific Instruments, Vol. 36, No. 5, p. 646–653 (1965), U.S. Pat. No. 4,580,093 to Feier et al, U.S. Pat. No. 5,247,461 to Berg et al, and U.S. Pat. No. 5,452,237 to Jones, Jr.

Most count correction methods rely on only one technique to perform the correction. It would be better to utilize more than one technique to allow for more gentle correction from each one with a more linear (accurate) final result.

SUMMARY OF THE INVENTION

This present invention relates to an improved particle count correction method with better particle count linearity (better accuracy) for samples with wide variation in particle sizes and wide variations in concentrations (high concentrations often produce lower accuracy).

This is accomplished by providing a method for counting particles, comprising the steps of successively passing multiple particles through a particle sensing zone; introducing a first signal into said particle sensing zone for a period of time; measuring a second signal emanating from said particle sensing zone, said second signal being caused by modulation of said first signal by said particles passing through said particle sensing zone; generating raw data using said second signal, said raw data correlating to a raw count of particles passing through said chamber, a wait time count and a size of each particle; and processing said raw data by using a true average flight time and a true average wait time to obtain a corrected count of particles.

In another embodiment, the invention is directed to an apparatus for counting particles in a sample, comprising one or more particle sensors, each sensor having a sensing zone; a particle delivery unit for delivering particles to at least one of said particle sensing zones, said particles passing through at least one sensing zone; a particle measuring unit for determining the size of particles passing through at least one of said particle sensing zones, said sensor generating a particle size signal, and for determining the number of particles that pass through at least one of said particle sensing zones in a given period of time, said particle sensor generating a particle number signal; a device for calculating the average flight time of said particles in said sample based on said particle size signal and said particle number signal; and a correcting unit for correcting an apparent particle count to an adjusted particle count by adding a true average flight time to a true average wait time to obtain a corrected count of particles.

In still another embodiment, the invention is directed to an apparatus for counting particles, comprising a chamber having an inlet, an outlet and a particle sensing zone located between said inlet and said outlet; a pump for passing a fluid containing particles into said inlet, through said particle sensing zone and out of said outlet; an electric source arranged to pass an electric current through said particle sensing zone; an electric current detector for measuring electric current as particles pass through said particle sensing zone, said detector generating raw data indicative of the number of particles passing through said particle sensing zone and indicative of the size of particles passing through said particle sensing zone; and a program for processing raw data from said detector, said program having the capability add true average flight time to average wait time to give a true average period value.

In yet another embodiment, the present invention improves the wait time count correction method by adding the true average flight time to the average wait time to give a true average period value which will yield a more accurate count for samples with a wide range of cell sizes such as white blood cells. This is more accurately an average period count correction method. The true average flight time is derived from the mean value of the size histogram of the sample population and a formula which relates the particle flight time to mean size. This formula is empirically derived from the counting instrument and is a function of aperture size, particle size, and flow rate.

This method also uses both the Average Period Count correction method and an enhanced coincidence correction formula to correct the raw count. Adjustment factors FTCF, BaseZ, and CCRFT are used in their respective methods to adjust the amount of correction each one has on the count.

Average Period Correction Method Formula:

APC=Average Period Count

CT=Count Time in seconds

RC=Raw Count for one CT or the average from multiple CT's.

WTC=Wait Time Count for one CT or the average from multiple CT's.

CTClk=Count Time Clock in counts per second

AFT=Average Flight Time in microseconds, (Count conversion 10 is in units of counts per microsecond)

FTCF=Flight Time Correction Factor $$APC = \frac{RC}{\frac{WTC + FTCF*(RC*10*AFT)}{CTClk*CT}} \quad (3)$$

Enhanced Coincidence Correction Formula:

TC=True Count

APC=Average Period Count

BaseZ=Main factor for control of coincidence correction

CCRFT=Coincidence Correction Flight Time factor.

Z=BaseZ+(AFT*CCRFT) (includes correction for particle size)

$$TC = \frac{1}{Z}\ln\left(\frac{1}{1-(Z*APC)}\right) \quad (4)$$

BRIEF DESCRIPTION OF THE DRAWINGS

FIG. 2A is a pulse diagram showing the interaction of different size particles and coincidence in the aperture waveforms and identifies the corresponding flight time pulse width and wait time, as well as the corresponding count and wait time count;

FIG. 2B depicts the Digital Count pulse.

FIG. 2C depicts the Clock pulse.

FIG. 2D depicts the Wait Time Count Clock pulse.

DETAILED DESCRIPTION OF THE INVENTION

Definitions

Figure 1:
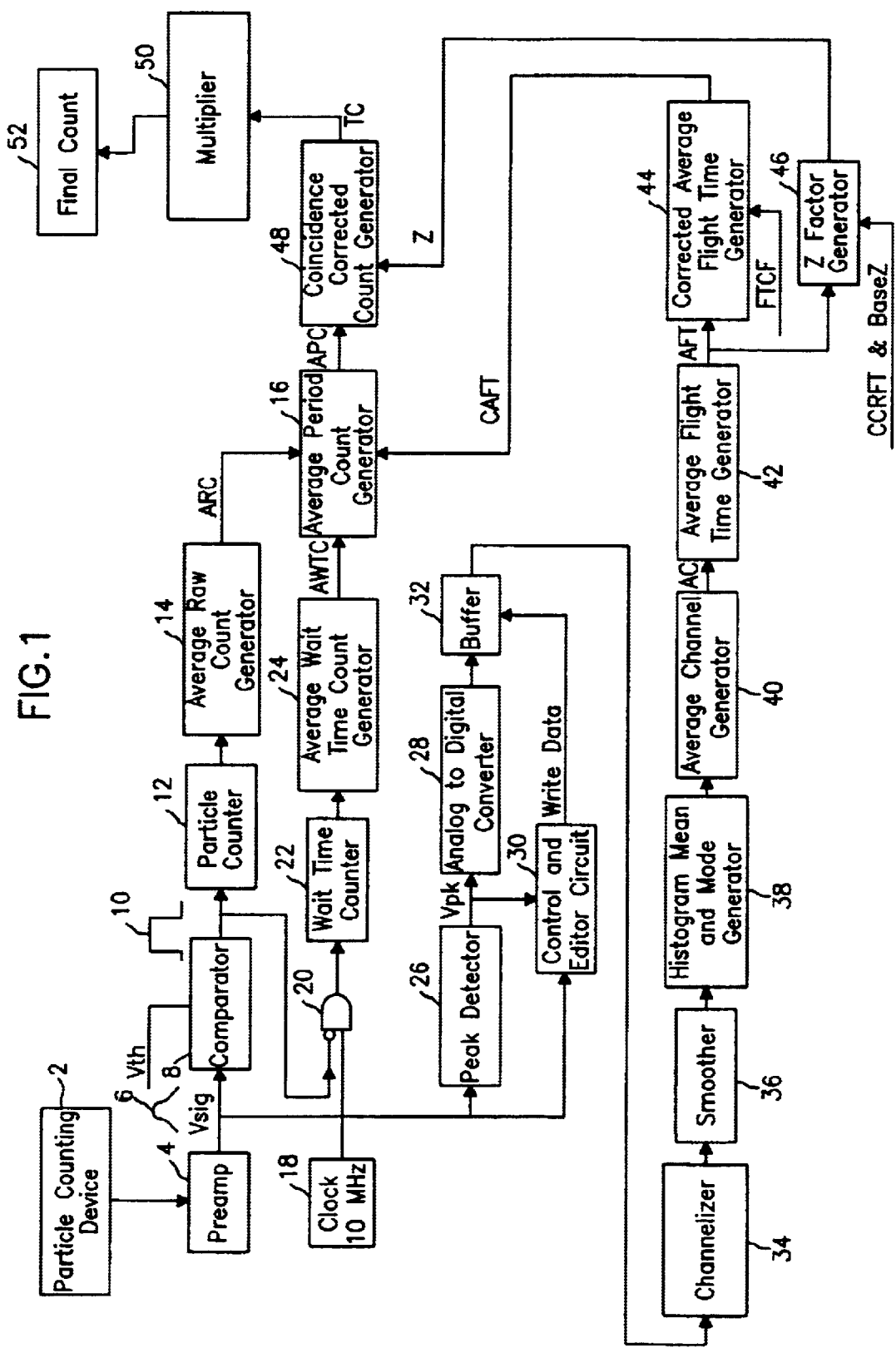
FIG. 1 depicts the various operational units of a preferred embodiment of the device.

In the present application, unless the context indicates otherwise, the following terms and abbreviations have the following meanings.

Average Period Method: A method for correcting particle counts where high levels of coincidence loss are present. It generates the corrected particle count from the inverse of the derived average period of the particles counted. It will automatically correct the count when different size particles are run in the instrument. This method performs well until the particle concentration becomes very high.

Enhanced Coincidence Correction Method: A method for correcting particle counts where high levels of coincidence loss are present. It generates the corrected particle count from a standard coincidence correction algorithm that has been enhanced to include the average flight time to allow adjustment of the amount of correction required based on particle size. It will automatically correct the count when different size particles are run in the instrument. This method performs well by itself on the raw count until the concentration becomes very high.

Average Period Count (APC): The corrected particle count derived from the average period correction method. This uses the raw count, the wait time count, and the size histogram to correct the raw count.

True Coincidence Corrected Count (TC): The corrected particle count derived from the enhanced coincidence correction method. To improve linearity and accuracy, it is applied to the Average Period Count.

Final Count: The true count is multiplied by the scaling factor (DR/FR) and calibration factors to yield the final particle count result in counts per $\mu L$.

Correction Factors (FTCF, BaseZ, CCRFT): These correction factors are empirically determined in parallel by using various size latex bead solutions at various concentration levels as well as blood control material. Only one size of bead is used per test solution. They are adjusted until the count linearity is optimized for the various size test particles. For any instrument there are numerous sets of proportional values, which yield acceptable results. Different instruments will require different factors depending on the aperture size, particle size, and flow rate. Some example of correction factors include:

Flight Time Correction Factor (FTCF): This factor adjusts the amount of correction performed by the average period method.

BaseZ: This factor adjusts the amount of correction performed by the coincidence correction algorithm.

Coincidence Correction factor from the Flight Time (CCRFT): This factor adjusts the amount of correction of the coincidence correction algorithm using the derived average flight time.

Count Time (CT): The time that particles are counted in the aperture. This method has a preferred count time of one second that is repeated from 4 to 10 times depending on whether the histogram sizing is complete. However, other suitable count times well known in the art may also be used. Having information about counts per second is very useful in debugging problems. Also, it is possible to eliminate counts that are significantly different than the rest. This eliminates intermittent problems due to bubbles or clogs.

Raw Count (RC or ARC): The total count in a counter that is incremented by the rising or falling edge of the count pulse for exactly 1 count time. The raw count is depicted in FIG. 2B. This counter is buffered and reset at the end of each second. The system then reads each of the buffered values. If the count time is repeated multiple times then this value can be the average of the multiple counts.

Count Time Clock (CTClk): The clock used to increment the wait time counter when no particle is present in the aperture sensing zone. This is in units of counts per second. For example, a 10 MHz clock CTClk=10,000,000 counts/second. An example of a graphical depiction of the 10 MHz clock pulse is shown in FIG. 2C. It is used to convert the wait time count into seconds.

Wait Time: The time spent waiting for the next particle after the current particle has exited the aperture sensing zone. This is the time between two particles when no particle is sensed in the aperture and the count signal is low, as is shown in FIG. 2A.

Wait Time Count (WTC): The total count from a counter that is enabled to increment the count from a fixed frequency clock when no particle is present in the aperture during the count time. If the count time is repeated multiple times then this value can be the average of the multiple counts. A graphical depiction of the Wait Time Count with respect to the digital count pulse and Count Time Clock is shown in FIGS. 2B–2D.

Total Wait Time (TWT): The total time that no particle of sufficient size is in the apertures effective sensing volume during the count time. This is the sum of all the spaces between the analog pulses that cross the threshold. TWT=WTC/CTClk. This is a measurement of the total time between the particles as it is not corrupted at high concentrations like the flight time.

Flight Time (Pulse Width) (FT): The time that a particle is sensed in the apertures effective sensing volume such that the resulting analog pulse is above the count threshold. As is shown in FIG. 2A, this is the time that a particle of sufficient size is sensed as it flies through the aperture. This is equivalent to the pulse width time of the analog pulse as measured at the points where the analog pulse goes above and then below the count threshold.

Flight Time Count (FTC): The total count from a counter that is enabled to increment the count from a fixed frequency clock when a particle is present in the aperture during the count time.

Total Flight Time (TFT): The total time that a particle of sufficient size is in the apertures effective sensing volume during the count time. This is the sum of all the analog pulse widths that cross the threshold. The typical formula is TFT1=FTC/(CTClk*CT). This measurement is corrupted by coincidence events at high concentrations and is not an adequate measurement of the true total flight time of the particles. This new invention method uses the Average Flight Time and the Raw Count to provide a more accurate estimate of the true total flight time. TFT2=(RC*10*AFT)/(CTClk*CT).

Average Channel (AC): This is the channel number (0 to 255) derived from the 256 channel size histogram. This channel number is representative of the average size of the particles that were counted.

Average Flight Time (AFT): This is the estimated true average flight time or pulse width of the particles that were counted. This is the average time that a particle pulse was above the count threshold. This is derived from the average channel and the empirically derived formula that converts the channel number to pulse width or flight time. It does not matter if the particles in a sample are of one size or have a wide size variation the average flight time value will linearize the count.

Z: This is the main adjustment factor used in the coincidence correction formula used in the method according to this invention. This is essentially equivalent to the average time that a particle is present in the aperture sensing zone. It is typically in units of micro seconds. This is determined by the ESV or effective sensing volume and the FR or Flow rate. The formula is $Z(s)=ESV(\mu L)/FR(\mu L/s)$.

Effective Sensing Volume (ESV): This is a volume in micro liters that consists of the effective aperture volume plus the increase in the effective volume due to the particle size. Because the particle is sensed before it is actually in the aperture the effective aperture volume looks larger. Larger particles will be in the sensing zone longer than smaller particles. This part of the volume is variable depending on the size of the particles. Typically, the average size of the particle is used. The enhanced method described does include correction for particle size variation.

Particle Samples

The present invention has particular application to counting particles in samples having high density (or a potential for significant density variability) and/or high particle size variability. For example, the invention is particularly useful for samples that have a particle concentration so high that the average time between particles is less than the flight time. Cell density as it flows through the aperture is ((450,000 counts/$\mu$L)/251)/1.12(Cal factor)=1600 cells per microLiter. White cells vary in size from 30 to 450 femtoliters. In the LH-750™ this corresponds to flight times of from 15 to 30 microseconds, respectively. The WBC flow rate is 40 microliters per second. The average particle count rate for a 450,000 WBC count blood is Count Rate=((WBC *FR)/DR)/Cal Factor=((450000 counts/$\mu$L*40 $\mu$L/s)/251)/1.12= 64,029. This corresponds to an average cell period if the cells went through the aperture evenly spaced of 1/64,029= 15.6 microseconds. At this high concentration it is clear that if the cells went through evenly spaced that only one cell would be sensed as they are too close together. The pulse width of the white cell is equal or greater than the average spacing between the cells. It is only because the cells are randomly spaced that a count can still be recovered. When both high density and high particle size variability are present in a sample, current methods can often render inaccurate particle number counts. However, the invention also works with samples having a substantially homogenous particle size distribution.

In a preferred embodiment, the particles to be counted are blood cells such as white blood cells and red blood cells. However, the present invention is applicable to counting many different types of particles, especially where particle size variability and particle density variability are expected. Examples of other types of particles that may be counted include latex particles and other biological or industrial particles. The preferred embodiment of the invention applies to counting single types of particles or cells of a certain minimum size and larger.

Counting platelets is especially difficult in that they usually have larger red cells present at the same time, which can significantly reduce the PLT count. The red cells cause a coincidence loss in the PLT counts when a PLT goes through the aperture with a red cell. In order to apply this invention to platelet counts when red cells are counted in the same bath, formula (4) needs to be modified to reflect the coincidence loss due to the presence of the red cells.

Figure 6:
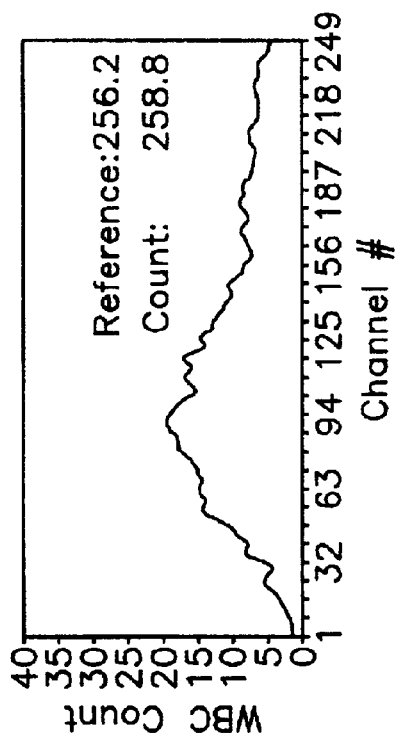
FIGS. 6–9 are WBC histograms for four different samples from data in FIG. 5 having an abnormally high WBC count.
Figure 7:
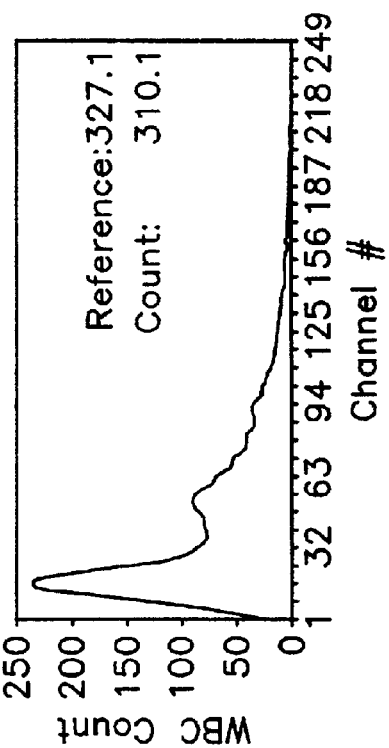
Figure 8:
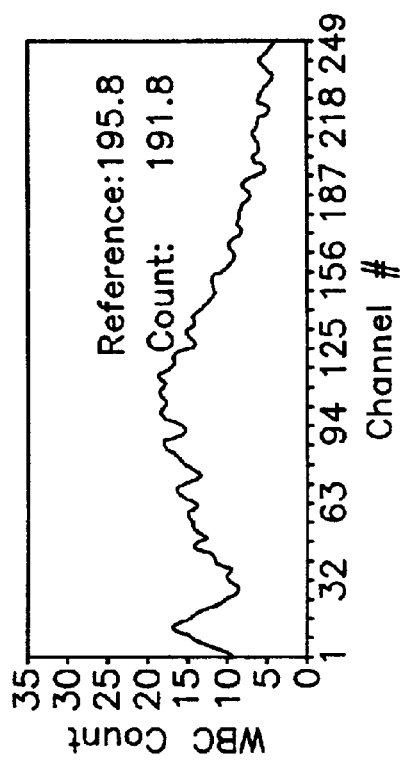
Figure 9:
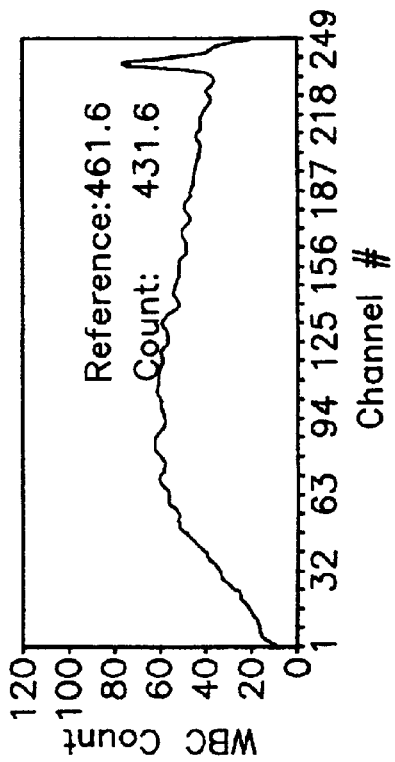

White blood cells are usually more variable in size than red blood cells and platelets, and therefore, the present invention has particular applicability in counting white blood cells. For example, in a "normal" blood sample (a sample from an individual that does not have an infection), white blood cells often vary in size by more than 50%, and can vary by more than 100% (with the smaller blood cells representing the baseline size for measuring variability). In abnormal bloods the white cells size can vary greatly depending on the nature of the illness. Some samples have small white cells as in FIG. 9 and some have large cells as in FIG. 8. See also FIGS. 6 and 7. Thus, the present invention allows more accurate counting of samples that have a wide variation (50 fL to 400 fL) in the size of the white cells.

In addition, the number of white blood cells (density) can vary greatly from a "normal" (uninfected) patient to an "abnormal" (infected) patient. For example, the number of white blood cells in an infected patient can be 90 times greater than the number of white blood cells in a normal patient. Thus, the present invention allows more accurate counting of samples that are expected to have concentration differences of 2 fold or greater, preferably 10 fold or greater, more preferably 75 fold or greater, and even 100 fold or greater. Thus, the particle counter can accurately count white blood cells in a low density sample (from a normal individual) and in a high density sample (from an infected individual) under the same testing conditions. This prevents having to rerun a sample through a machine (after dilution) if abnormally high numbers of cells are detected in order to obtain a more accurate reading.

Preferred Embodiment

As shown in FIG. 1, a sensor in a particle counting device 2 makes measurements relating to the size of particles in a particle sensing zone and the number of particles that pass through the particle sensing zone in a given period of time. The sensor may be in a particle counting device 2 such as a COULTER COUNTER® or other suitable particle counting device well known in the art. In such a device, particles suspended in an electrically conductive medium (usually an aqueous salt solution) are measured by passing the particle suspension through a small orifice or aperture through which an electric current is flowing. This is the particle sensing zone. A particle passing through the particle sensing zone produces a decrease in conductivity; the sensor converts the conductivity changes to a voltage pulse (particle pulse signal), which can be counted (see FIGS. 2A and 2B). The magnitude (amplitude) of the pulse is nearly proportional to the volume of the particle. If two particles pass through the particle zone at the same time (or too close together), the two particles can be counted as a single particle (See FIG. 2A). This is known as "coincidence loss".

Each COULTER COUNTER or other particle counting device may have one or more apertures and a sensor corresponding to each aperture.

The sensor in the particle counting device 2 is connected to a preamp 4, which receives the output particle pulse signal generated by the sensor. The preamp 4 amplifies the signal and generates an analog voltage signal Vsig 6. The preamp 4 is also connected to a comparator 8, peak detector 26 and control and editor circuit 30.

The comparator 8 is connected to the preamp 4, AND gate 20, and particle counter 12. The comparator 8 receives Vsig 6 from preamp 4 and compares Vsig 6 to a threshold Vth (shown in FIG. 2A) and generates digital signal 10 representing the portions of Vsig above the threshold Vth. The digital signal 10 of the comparator 8 is received by the particle counter 12 and the AND gate 20.

The particle counter 12 is connected to comparator 8 and average raw count generator 14. The particle counter 12 generates a raw count that is incremented by the rising or falling edge of each pulse in signal 10.

The average raw count generator 14 receives the output raw count from the particle counter 14 and generates an average raw count ARC.

A clock 18, which is preferably a 10 MHz clock, is connected to the AND gate 20. The AND gate receives signal 10 from comparator 8 and signals from the clock 18. The AND gate 20 outputs a signal from the clock 18 when digital signal 10 allows the clock signal to pass through the AND gate 20.

The wait time counter 22 is connected to AND gate 20 and the average wait time count generator 24, and when the clock signal is output from the AND gate, the wait time counter 22 increments to generate a wait time count.

The average wait time counter 24 is connected to the wait time counter 22 and the average period count generator 16. The average wait time count generator 24 receives the wait time count from the wait time counter 22 and generates an average wait time count AWTC.

The peak detector 26 is connected to preamp 4, control and editor circuit 30 and analog to digital converter 28. The peck detector receives Vsig 6 from preamp 4 and outputs the amplitude of a peak value of the pulses Vpk to the analog to digital converter 28. Vsig and Vpk are also outputted to the control and editor circuit 30.

The control and editor circuit 30 is connected to the peak detector 26 and buffer 32. The control editor circuit 30 receives and compares Vpk and Vsig to edit the pulses by suitable techniques well known to those of ordinary skill in the art. The control and editor signal generates a write pulse for good cells to store only the size data of good cells in data buffer 32.

Digital converter 28 is connected to buffer 32 and receives the Vpk data and generates digital size data, which is stored in data buffer 32.

Data buffer 32 is also connected to the channelizer 34, which may read the data stored in buffer 32, such as the digital size data of good cells, to generate a channelized size histogram. Examples of the channelized size histograms are provided in FIGS. 6–9.

The channelizer is also connected to smoother 36, which receives the channelized size histogram from the channelizer 34 and smooths the histogram.

A histogram mean and mode generator 38 is connected to the smoother 36 and average channel generator 40. The histogram mean and mode generator 38 receives the smoothed histogram from the smoother 38 and generates an estimate of the average population size.

The average channel generator receives the estimate of the average population size from the histogram mean and mode generator 38 and outputs an average channel size AC.

The average flight time generator 42 is connected to the average channel generator 40, the Z factor generator 46 and the corrected average flight time generator 44. The average channel size AC is received as an input to the average flight time generator 42 and the average flight time generator 42 converts the average channel size into an average flight time per pulse AFT.

The average flight time AFT is then received by both the corrected average flight time generator 44 and the Z factor generator 46. The corrected average flight time generator 44 multiplies the average flight time AFT by the flight time correction factor stored therein and generates the corrected average flight time CAFT.

The average period count generator 16 is connected to the corrected average flight time generator 44, average raw count generator 14 and the average wait count generator 24 and uses the outputs of all three generators 44, 14 and 24 to calculate an average period count APC.

The Z factor generator is connected to the average flight time generator 42 and the coincidence corrected count generator 48 and receives the average flight time AFT from the average flight time generator 42 and also receives inputs of the coincidence correction factor from the flight time CCRFT and BaseZ factor. Using these inputs, the Z factor generator calculates the Z factor and outputs the Z factor to the coincidence corrected count generator 48.

The coincidence corrected count generator 48 is connected to the average period count generator 16 as well as the Z factor generator 46, and receives the average period count APC output by the average period count generator 16 and the Z factor output by the Z factor generator 46. Using the average period count APC and the Z factor, the coincidence corrected count generator 48 performs coincident correction calculations on the data and outputs a true count TC.

The true count is received by multiplier 50 which is connected to the coincidence corrected count generator 48. Multiplier 50 converts and scales the data to generate a final count 52 of the counted particles such as white blood cells in the sample.

As discussed above, the particle sensor maybe part of a COULTER COUNTER or other suitable particle counting device 2 well known in the art. The preamp 4, comparator 8, particle counter 12, clock 18, AND gate 20, peak detector 26, analog to digital converter 28, and control and editor circuit 30 also may be part of the COULTER COUNTER or other suitable particle counting device as hardware components. The wait time counter 22 may be a hardware or software component operated by microprocessor within the COULTER COUNTER or other suitable particle counting device. The average raw count generator 14, average wait time count generator 24, average period count generator 16, channelizer 34, smoother 36, histogram mean generator 38, average channel generator 40, average flight time generator 42, corrected average flight time generator 44, Z factor generator 46, coincidence corrected count generator 48, and multiplier 50 are software applications which are embodied and performed in a computer system, computer or microprocessor associated with the COULTER COUNTER or other suitable particle counting device.

It is noted that the invention may alternatively have various embodiments as would be known to one of ordinary skill in the art. For example, instead of hardware, software applications could be utilized for each of the comparator 8, particle counter 12, peak detector 26, control and editor circuit 30, and wait time counter 22. Further, the software applications may be embodied in one or more computer processors or microprocessors.

The following represents an example of how a preferred method of the operation of the invention can be applied to the WBC parameter in an LH-750 with three apertures. It can be applied just as well to other parameters, i.e., RBC, any number of apertures, and other suitable particle containing devices.

The method is described with respect to one aperture of three apertures in the LH-750. However, similar processing is performed for each aperture. The data from each aperture is later combined by multiplier 50 as discussed below to generate the final count.

Step 1: Get Raw Count and Wait Time Count Data

As shown in FIG. 1, a sensor in a particle counting device 2 generates waveform signals (particle pulse signals) corresponding to particles passing through an aperture in the sensor (see also FIGS. 2A–2D). The voltage waveform signal represents the particle passing through the aperture as a function of time. The voltage is affected by the size of the particles. The waveform signals from the sensor are fed through a preamp 4 to amplify the signal up to about 10 volts. An amplified analog voltage signal 6 (Vsig) is sent from the preamp 4 to the comparator 8 where the analog signal is converted to a digital signal 10. All signals that fall below a certain voltage threshold (Vth), as shown in FIG. 2A, are filtered out in the comparator 8. Signals 10 from the comparator 8 are sent to a particle counter 12 to generate a raw count where particles are counted for one second of count time. The average raw count generator 14 uses the raw count from the particle counter 12 to generate an average RC. The average RC is calculated by averaging multiple raw counts (such as 4–10 raw counts). For example, four 1-second raw counts or ten 1-second raw counts can be averaged to generate an average RC.

The average RC is then used as one of 3 inputs to generate an average period count (APC). Note: Any individual one second values may be excluded based on being non-uniform as compared to the other values.

Digital signals 10 from comparator 8 are also used to enable the count time clock 18 (i.e., 10 MHz constant frequency clock) to pass through AND gate 20 and increment the wait time counter 22 when digital signal 10 is low or zero volts indicating that no particle of sufficient size is in the sensing zone. The value in the counter at the end of the count time is the Wait Time Count. The average wait time count generator 24 uses the wait time count from the wait time counter 22 to generate an average WTC. The average WTC is calculated by averaging multiple wait time counts (such as 4–10 wait time counts). For example, four 1-second wait time counts or ten 1-second wait time counts can be averaged to generate an average WTC. The average WTC is then used by the average period count generator 16 as one of 3 inputs to generate an average period count (APC). Note: Any individual one second values may be excluded based on being non-uniform as compared to the other values.

This is different from the previously referenced U.S. Pat. No. 4,447,883 at least in that the time between particles is directly measured instead of deriving the time by subtracting the measured total flight time from the total count time.

Step 2: Correct the Raw Count Value Using the Average Period Method.

The average flight time (AFT) or average pulse width cannot be derived from the measured Total Flight Time and the raw count like the wait time can. The measured total flight time is corrupted because of the coincident particles that go through the aperture at the same time. In order to calculate the average flight time the average cell size must first be estimated.

In order to accomplish this, the analog signal 6 is sent to a peak detector 26 which stores the peak value (Vpk) or amplitude of any pulse. The amplitude of an analog pulse is proportional to particle size. The Vpk is sent to an analog to digital converter 28 where a digital signal is generated which is proportional to the analog Vpk value. The analog signal 6 and Vpk are also sent to a control and editor circuit 30 where real time signals are compared with peak signals to perform editing of the pulses. This editing process is well known in the industry and will eliminate those particles that have abnormal analog waveforms. See, for example, U.S. Pat. No. 3,710,264 incorporated herein by reference. This helps make the size histogram a true representation of the sample population that was counted. A write data signal is only pulsed for good cells and therefore bad cells are rejected and not written to the data buffer 32. The digital size value from converter 28 is stored in the data buffer 32 when the write data signal from circuit 30 is pulsed. Data buffer 32 stores the size information of each good cell as determined by the control and editor circuit 30.

The channelizer 34, smoother 36, histogram mean and mode generator 40, and average channel generator 40 operate using methods well known to those of ordinary skill in the art.

The stored digital size data from the buffer 32 is read and channelized into a size histogram by channelizer 34. The channelizer 34 scales the digital size value and uses the scaled digital size to select and increment one of the bytes or channels in a 256 byte array. This generates the size or frequency histogram. Examples of size histograms are depicted in FIGS. 6–9.

The average mean size of all particles that went through the sensing zone can be calculated from the channelized histogram of all the particles as indicated at 34. Smoother 36 smooths the size histogram using any suitable standard smoothing algorithm.

Mean and mode values are generated from the smoothed histogram by the histogram mean and mode generator 38 using equations 5 and 6 below. However, any method known to those of ordinary skill in the art which yields a suitable estimate of the true population size can be used. In this example, the average of the histogram mode and mean channel is used. The average channel generator 40 uses equation 7 to generate the average channel. This calculation corrects for the distortion in the histogram due to coincidence and signal conditioning. The goal is to get the best estimate possible of the true average size of the particles that are counted.

$$AMDC = \text{Average Mode Channel} = (Ap1\text{Max}Ch(0.255) + Ap2\text{Max}Ch(0.255) + Ap3\text{Max}Ch(0.255))/3 \tag{5}$$

$$AMNC = \text{Average Mean Channel} = (Ap1\text{Mean}Ch(0.255) + Ap2\text{Mean}Ch(0.255) + Ap3\text{Mean}Ch(0.255))/3 \tag{6}$$

$$AC = \text{Average Channel} = (AMDC + AMNC)/2 \tag{7}$$

The average flight time generator 42 converts the Average Channel to the Average Flight Time per pulse using an empirically derived formula. The relationship between particle size and particle pulse width should be characterized for a particular aperture size and flow rate. Various size particles are run through the instrument and the relationship between the particle size and pulse width is characterized. These values would be instrument related as each instrument may have different bandwidths and throughput which would affect the pulse width time. Each system may have a different characteristic relationship between the particle size and the Pulse width time.

Various formulas can be used for Average Channel AC to Average Flight Time AFT conversion. Two exemplary formulas are:

$$AFT=15.47+(AC/13.7) \text{ and} \quad (8a)$$

$$AFT=7.3983*Ln(AC)-10.431 \quad (8b)$$

The corrected average flight time generator 44 multiplies the Average Flight Time by the FTCF correction factor to yield the CAFT or Average Corrected Flight Time. This calculation is exemplified by equation 9.

FTCF=Flight Time Correction Factor=0.59 (This was empirically determined with latex beads using the Beckman Coulter LH-750. This allows the amount of the correction to be adjusted. However, other suitable Flight Time Correction Factors may be utilized.)

$$CAFT=\text{Corrected Average Flight Time}=FTCF*AFT=0.59*AFT \quad (9)$$

The CAFT generated by the Average Flight Time Generator is one of three inputs that are used to calculate the APC value by Average Period Count Generator 16.

The Average Period Count Generator 16 generates the APC values using the following formulas. The Average Period Count general formula is $$APC=ARC(\text{Average Raw Count from 14})/APT(\text{Average Period Time}).$$

The Average Period Time formula is $$APT=TWT(\text{Total Wait Time})+TFT2$$

where

TWT=Total Wait Time=WTC(from 24)/(CTClk*CT) and

TFT2=Total Flight Time=(CAFT(from 44)*10*RC (from 14)/(CTClk*CT).

Since the CAFT is in microseconds, it must be multiplied by 10 to get units of 100 ns which the wait time count is in. Alternately the APT formula can be written as $$APT=(WTC+(CAFT*10*RC))/(CTClk*CT).$$

The Final Formula that is used by the Average Period Count Generator 16 is:

$$APC=RC/((WTC+(CAFT*10*RC))/(CTClk*CT)) \quad (10)$$

Step 3: Coincidence Correct the Average Period Corrected Count.

Further correction of the data is obtained by using APC and Z and performed by the Coincidence Corrected Count Generator 48.

The Z factor is the main adjustment factor and is generated at by the Z factor generator 46 using equation 11.

$$Z=\text{BaseZ}+(AFT*CCRFT)=34.35*10^\wedge-6+(AFT*-0.3*10^\wedge-6), \quad (11)$$

where

BaseZ=Z base value=34.35*10^-6 (empirically determined with latex beads)

AFT=Average Flight Time from step 2 (42 in FIG. 1)

CCRFT=Coincidence correction factor from flight time=-0.3*10^-6 (empirically determined with latex beads)

Although the Z base value and Coincidence Correction factors are empirically determined, these factors are examples of suitable correction factors, and other suitable factors may be used.

The coincidence corrected count generator 48 generates a True Count TC using equation 12.

$$TC = \frac{1}{Z}\ln\left(\frac{1}{1-Z*APC}\right), \quad (12)$$

wherein

TC=True coincidence corrected Count, and

APC=Average Period Count

Multiplier 50 receives the True Count TC from the Coincidence Corrected Count Generator 48. Although FIG. 1 indicates only one line 54 from the Coincidence Corrected Count Generator 48 to Multiplier 50, the Multiplier receives a True Count TC corresponding to each aperture. In the embodiment described, there are three apertures. The Multiplier 50 receives three True Counts. In other embodiments, the number of True Counts TC received by the multiplier could be more or less than three.

Step 4: Scaling, Matching, Averaging and Final Count.

The Multiplier 50 performs calculations on the True Counts TC from each aperture to generate the final count 52. The calculations include scaling, matching and averaging the data by methods well known to those of ordinary skill in the art.

The data is converted back to count/µl by multiplier 50, so that it is in a form that is convenient or usable. Other conversions to other forms may also be performed as needed. Values from multiple channels (if present) are averaged. A final count representative of the total number of white blood cells in the sample is obtained as shown at final count 52.

Figure 3:
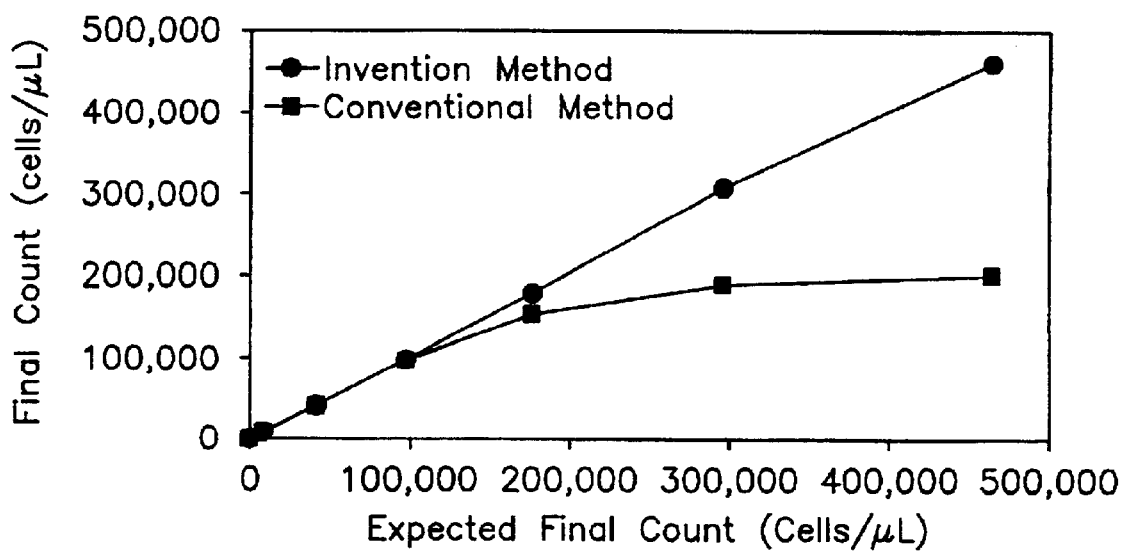
FIG. 3 is a graph that shows the improved linearity of one embodiment of the inventive method when compared to another conventional method using a readily available WBC linearity control material.
Figure 4:
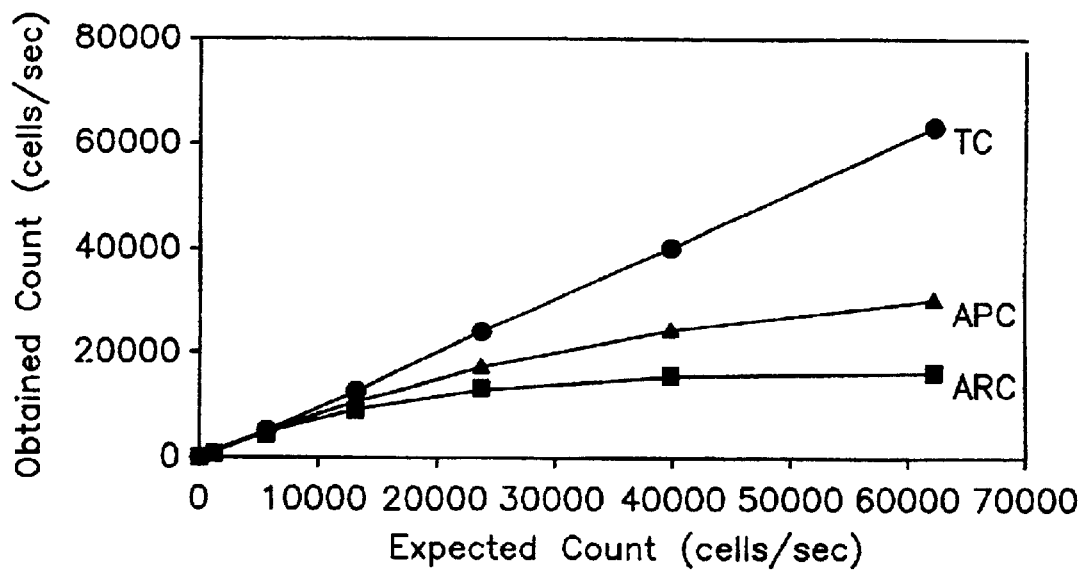
FIG. 4 is a graph that illustrates the average Raw Count (ARC) values and the results obtained after applying each method using the same data as FIG. 3. APC shows the effect that the average period method has on ARC. TC shows the results of applying the enhanced coincidence correction method to APC.
Figure 5:
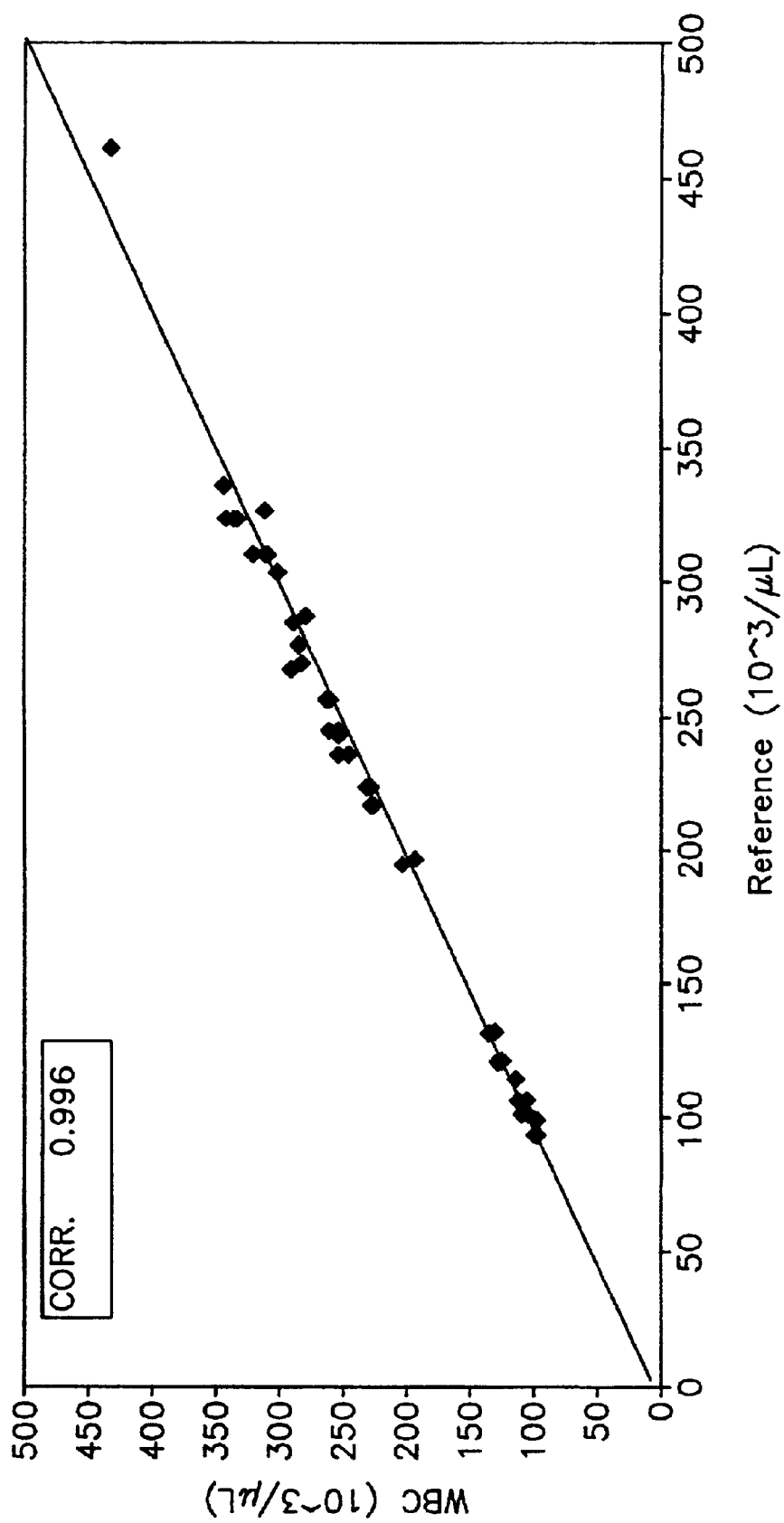
FIG. 5 shows the correlation between the method of the invention and a reference method for abnormally high WBC blood samples. The reference method values were obtained by pre-diluting the samples and running them on a Beckman Coulter, Inc. GEN*S™. The values using the present invention were obtained from a Beckman Coulter, Inc. LH-750™ instrument without dilution.

The Average Period count correction method is more accurate than previous methods. It takes into consideration the effects of particle size in the correction formula so that it is linear, as is shown in FIG. 3 (which corresponds to accuracy), no matter what size of particle is run in the system. By using this method with an enhanced coincidence correction formula, the count linearity can be maintained even at very high sample concentrations such as are found in high 450K white blood samples. By allowing the concentration to be this high, the throughput of the instrument is kept high. Throughput and accuracy can be achieved with current technology which is adapted to use the above-described correction method.

The invention is not limited to the above embodiments. For example, in the above embodiment, averaging of multiple count times occurs on the raw data in the Average Raw Data Count Generator 14 and Average Wait Time Count Generator 24. These averaging steps could also be performed at the Average Period Count Generator 16 or after the Coincidence Corrected Count Generator 48 and even at the final count 52. Four to 10 Average Period Count APC Values could be calculated from the raw data and then averaged; four to 10 true count TC values could be calculated and averaged; or, four to 10 final count values could be calculated and then averaged.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for counting particles, comprising the steps of:
   successively passing multiple particles through a particle sensing zone in the form of an orifice through which an electric current is flowing;
   introducing a first electrical signal into said particle sensing zone for a period of time;
   measuring a second electrical signal emanating from said particle sensing zone, said second electrical signal being caused by modulation of said first electrical signal by said particles passing through said particle sensing zone;
   generating raw data using said second electrical signal, said raw data correlating to a raw count of particles passing through said particle sensing zone, a wait time count and a size of each particle;
   calculating a true average fight time using said size of each particle; and
   processing said raw data by using said true average flight time and a true average wait time to obtain a corrected count of particles.

2. The method of claim 1, wherein said particles are biological particles.

3. The method of claim 1, wherein said particles are blood cells.

4. The method of claim 1, wherein said particles comprise white blood cells.

5. The method of claim 1, wherein a sample containing multiple particles of sizes varying by more than 50% is passed through said measuring chamber.

6. The method of claim 5, wherein said sample has a particle concentration so high that the average time between particles is less than the flight time.

7. The method of claim 1, wherein said particle sample is one which is expected to have a particle density variability of greater than 50 fold between various different samples.

8. The method of claim 1, wherein the true average flight time corresponds to a true average time that said second signal is above a threshold using said size of each particle.

9. The method of claim 1, wherein the true average wait time corresponds to a true average time that particles are absent from the sensing zone.

10. The method of claim 1, further comprising using an average period correction method calculation and an enhanced coincidence correction calculation to correct raw data to account for particle size variability in said sample.

11. An apparatus for counting particles in a sample, comprising:
   one or more particle sensors, each sensor having a sensing zone;
   a particle delivery unit for delivering particles to at least one of said particle sensing zones, said particles passing through at least one sensing zone;
   a particle measuring unit for determining the size of particles passing through at least one of said particle sensing zones, said sensor generating a particle size signal, and for determining the number of particles that pass through at least one of said particle sensing zones in a given period of time, said particle sensor generating a particle number signal;
   a wait time measuring unit which measures the time there are no particles in at least one of the sensing zones in a given period of time;
   a device for calculating a true average flight time of said particles in said sample based on said particle size signal; and
   a correcting unit for correcting an apparent particle count to an adjusted particle count by adding a true average flight time to a true average wait time to obtain a corrected count of particles.

12. An apparatus for counting particles, comprising:
   a chamber having an inlet, an outlet and a particle sensing zone located between said inlet and said outlet;
   a pump for passing a fluid containing particles into said inlet, through said particle sensing zone and out of said outlet;
   an electric source arranged to pass an electric current through said particle sensing zone;
   an electric current detector for measuring electric current as particles pass through said particle sensing zone, said detector generating raw data indicative of the number of particles passing through said particle sensing zone, indicative of a true wait time, and indicative of the size of particles passing through said particle sensing zone; and
   a program for processing raw data from said detector, said program calculating a true average flight time using the size of the particles, calculating a true average wait time from the true wait time divided by the number of particles passing through said particle sensing zone and adding said true average flight time to true average wait time to give a true average period value whose inverse value is a corrected count.

13. The apparatus of claim 12, wherein said program uses an average period correction method calculation and an enhanced coincidence correction calculation to correct raw data obtained from said detector to account for particle size variability in said sample.

14. A method for counting particles, comprising the steps of:
   successively passing multiple particles through a particle sensing zone;
   introducing a first signal into said particle sensing zone for a period of time;
   measuring a second signal emanating from said particle sensing zone, said second signal being caused by modulation of said first signal by said particles passing through said particle sensing zone;
   generating raw data using said second signal, said raw data correlating to a raw count of particles passing through said chamber, a wait time count and a size of each particle;
   calculating a true average flight time using said size of each particle; and
   performing coincidence correction by processing said raw data by using a said true average flight time.

15. A method for determining the actual number of particles in a sample containing a plurality of particles of varying size; comprising the steps of:
   I. passing the particles sequentially through a raw counting device which produces an analog voltage signal;
   II. converting said analog voltage signal to a digital signal comprising a plurality of series of voltage pulses wherein each pulse is caused by the passage of one or more particles through the raw counting device; wherein each series has a beginning and an end wherein the time difference between said beginning and said end is defined as the duration of each series wherein the time between series is defined as wait time;

III. converting the peak of the analog voltage signal to digital particle size data;

IV. converting digital particle size data into a size frequency graph;

V. generating an average channel size from said particle size frequency graph;

VI. converting said average channel size into a true average flight time;

VII. converting the raw wait time to a true average wait time;

VIII. employing the true average flight-time and the true average wait time to calculate the actual number of particles in a sample.

16. An apparatus for determining the actual number of particles in a sample containing a plurality of particles of varying size, said apparatus comprising:

A. a particle counting device which produces a weak analog signal being a series of low voltage pulses;

B. a preamp which receives said weak analog signal from the particle counting device; amplifies the weak analog signal and produces a voltage signal (Vsig);

C. a comparator which receives said voltage signal (Vsig) from the preamp and compares said voltage signal (Vsig) with a predetermined voltage threshold (Vth) and produces a digital output signal being a series of digital pulses wherein the voltage signal had a voltage greater than the predetermined voltage threshold (Vth);

D. a raw particle count generator which receives the digital output signal from the comparator and produces a raw count of the number of particles;

E. an average raw count generator which receives the raw count of the number of particles from the raw particle count generator, and averages them thereby producing an average raw count;

F. a megahertz clock which produces a clock signal;

G. an AND gate which receives the clock signal from the megahertz clock and the digital output signal from the comparator and produces a digital output signal comprising a series of digital clock pulses when the digital out signal is low indicating the signal Vsig is below the threshold Vth;

H. a raw wait time counter which receives the digital output signal from the AND gate determines a raw wait time between adjacent series of pulses thereby producing a wait time count;

I. a corrected average flight-time generator which receives information based on said voltage signal (Vsig) peak from the preamp and produces a corrected average flight-time;

J. an average period count generator which receives:
 1. the average raw count from the average raw count generator;
 2. an average wait time from an average wait-time count generator; and
 3. the corrected average flight-time from the corrected average flight-time generator;
 and which employs the average raw count; the average wait-time; and the corrected average flight-time to produce an average period count;

K. a coincidence-corrected count generator which receives the average period count from the average period count generator and which also receives an empirically determined correction factor; and then applies an enhanced coincidence correction formula and the empirically determined correction factor to the average period count, thereby determining a true count of the number of particles in the sample.

* * * * *